(12) United States Patent
Sundman et al.

(10) Patent No.: US 7,895,009 B2
(45) Date of Patent: Feb. 22, 2011

(54) IMPRESSION FOAM DIGITAL SCANNER (75) Inventors: Arjen Sundman, Lake Oswego, OR (US); Jeffery L. Davis, Vancouver, WA (US)

(73) Assignee: Amfit, Inc., Vancouver, WA (US)

( * ) Notice: Subject to any disclaimer, the term of this patent is extended or adjusted under 35 U.S.C. 154(b) by 146 days.

(21) Appl. No.: 12/291,240

(22) Filed: Nov. 7, 2008

(65) Prior Publication Data

US 2009/0138234 A1    May 28, 2009

Related U.S. Application Data

(60) Provisional application No. 61/002,141, filed on Nov. 7, 2007.

(51) Int. Cl.
    G01B 11/25    (2006.01)
    G01B 11/24    (2006.01)
    G06F 19/00    (2006.01)
    G06F 17/40    (2006.01)

(52) U.S. Cl. ................. 702/104; 356/601; 356/610; 356/625; 382/100; 702/85; 702/167; 702/187; 702/189

(58) Field of Classification Search ............ 33/501, 33/511, 512, 545, 546, 547; 356/2, 601, 356/610, 625, 626, 634, 635; 382/100, 111; 702/1, 85, 104, 105, 127, 150, 158, 166, 702/167, 187, 189, 155
See application file for complete search history.

(56) References Cited

U.S. PATENT DOCUMENTS

| 2,325,490 | A |   | 7/1943  | Elftman ................... 353/80 |
| 4,238,147 | A |   | 12/1980 | Stern ....................... 354/77 |
| 4,286,852 | A |   | 9/1981  | Stern et al. ................ 354/77 |
| 4,508,452 | A |   | 4/1985  | DiMatteo et al. ........... 356/375 |
| 4,521,171 | A |   | 6/1985  | Noonan .................... 356/601 |
| 4,705,401 | A |   | 11/1987 | Addleman et al. .......... 356/376 |
| 4,737,032 | A |   | 4/1988  | Addleman et al. .......... 356/376 |
| 4,819,660 | A |   | 4/1989  | Smith ...................... 128/774 |
| 4,846,577 | A |   | 7/1989  | Grindon ................... 356/376 |
| 4,877,326 | A |   | 10/1989 | Chadwick et al. .......... 356/394 |
| 5,025,476 | A |   | 6/1991  | Gould et al. ................. 382/2 |
| 5,118,192 | A |   | 6/1992  | Chen et al. ................ 356/376 |
| 5,170,037 | A | * | 12/1992 | Van Amstel et al. ........ 250/235 |
| 5,371,375 | A |   | 12/1994 | Stern et al. ................ 250/561 |

(Continued)

OTHER PUBLICATIONS

International Search Report mailed Jan. 9, 2009 in the corresponding International application No. PCT/US2008/012554.

*Primary Examiner*—Edward R Cosimano
(74) *Attorney, Agent, or Firm*—Ohlandt, Greeley, Ruggiero & Perle, L.L.P.

(57) ABSTRACT

This disclosure provides for an impression scanner system having improved calibration having a housing and a calibration plate of known geometry. The calibration plate has a plurality of different shapes thereon. The system also has a radiation source for emitting radiation towards the shapes on the plate and a surface for reflecting images created by the radiation on the shapes. A sensor for receiving the images of the shapes as the plate moves relative to the housing is also provided. A processor compares known geometry of the plate to the images received by the sensor and calibrates the sensor based upon the known geometry and images to reduce system aberration and distortion.

24 Claims, 7 Drawing Sheets

U.S. PATENT DOCUMENTS

| | | | |
|---|---|---|---|
| 5,615,003 A * | 3/1997 | Hermary et al. | 356/3.03 |
| 5,671,055 A * | 9/1997 | Whittlesey et al. | 356/602 |
| 5,689,446 A * | 11/1997 | Sundman et al. | 702/167 |
| 5,706,419 A * | 1/1998 | Matsugu et al. | 345/420 |
| 5,753,931 A | 5/1998 | Borchers et al. | 250/559.22 |
| 5,815,275 A | 9/1998 | Svetcov et al. | 356/376 |
| 5,870,220 A | 2/1999 | Migdal et al. | 359/216 |
| 5,986,745 A * | 11/1999 | Hermary et al. | 356/3.03 |
| 6,089,108 A | 7/2000 | Lucas | 73/865.8 |
| 6,205,230 B1 | 3/2001 | Sundman et al. | 382/100 |
| 6,289,107 B1 | 9/2001 | Borchers et al. | 382/100 |
| RE37,740 E | 6/2002 | Chadwick et al. | 356/394 |
| 6,549,639 B1 * | 4/2003 | Genest | 382/100 |
| 6,829,377 B2 | 12/2004 | Milioto | 382/128 |
| 7,068,379 B2 | 6/2006 | Sundman et al. | 382/128 |
| 7,145,579 B2 | 12/2006 | Arai et al. | 345/690 |
| 7,262,862 B2 | 8/2007 | Klaveness | 345/419 |
| 7,392,559 B2 * | 7/2008 | Peterson | 12/1 R |
| 7,617,068 B2 * | 11/2009 | Tadin et al. | 702/139 |
| 2003/0212506 A1* | 11/2003 | Sundman et al. | 702/40 |
| 2006/0227337 A1* | 10/2006 | Sundman et al. | 356/601 |
| 2006/0283243 A1* | 12/2006 | Peterson | 73/172 |
| 2008/0075328 A1* | 3/2008 | Sciammarella | 382/108 |
| 2008/0097720 A1* | 4/2008 | Tadin et al. | 702/139 |
| 2010/0058855 A1* | 3/2010 | Tadin et al. | 73/172 |

* cited by examiner

IMPRESSION FOAM DIGITAL SCANNER

CROSS-REFERENCE TO RELATED APPLICATIONS

This application claims benefit of expired U.S. Provisional Patent Application Ser. No. 61/002,141 filed on Nov. 7, 2007, the contents of which are incorporated by reference herein.

BACKGROUND OF THE INVENTION

1. Field of the Invention

This disclosure relates to a system for obtaining and scanning an impression of the plantar surface of the foot. This disclosure further relates to a system for obtaining and scanning a contour of an impression of the plantar surface of the foot that uses a self-contained laser scanning technology to digitize the contour of the impression for orthotics manufacture. This disclosure further relates to a system for obtaining and scanning an impression of the plantar surface of the foot that uses a calibration plate that reduces aberration and distortion of the scanned image.

2. Description of Related Art

Traditionally, devices for the purpose of capturing the three dimensional (3-D) shape or contour of the plantar surface of the foot require a foam impression that is filled with plaster. The resulting plaster is used to produce a model of the subject foot of the patient. The model can then be measured using a pin digitizer or a laser scanner to accurately create a representation of the plantar surface of the foot for orthotics manufacture. Systems that use plaster are inconvenient, require numerous steps and are time consuming. The laser scanning systems, while not requiring plaster, are not generally self contained or efficient.

Systems using optical digitization of a three dimensional (3-D) contour using a camera coupled with a light source for triangulation are known. Typically, the light source is structured or beamed; a beamed source would include a laser line projected at a proscribed incident angle onto an object within the camera field of view. Optical digitization systems are typically calibrated to map observed line location to contour data. Placing a predefined geometrical object in the camera field of view and mapping each point in the image to the known location on the object can realize the calibration. The recorded image data is compared with the known geometry of the object in the field of view to determine and assign geometry values to the observed location in the camera's image data. In this fashion, the system learns how to derive geometric data from point locations in the camera image. That is, the digitization system is calibrated.

There are a number of variations of the above-discussed concept. For example, one variation uses a calibration plate disposed between the light source and the surface to be scanned. The light passing through the calibration plate forms a pattern, such as a matrix of lines, a grid pattern, dots, etc. on the surface to be scanned. Alternatively, the digitization system may use a polar axis rather than a linear axis for the transport of the object being measured through the field of view of the camera and the structured light source. Such systems often have problems related to aberration and distortion of the image that is viewed by the camera, as well as inconsistency in brightness due to distance and angle of reflection.

Systems using the basic optical digitization discussed above are known. However, heretofore such systems have been large, expensive to build time and consuming to operate. This and other disadvantages limit the application of the laser scanning technology to applications where expense and size are not relatively important factors such as applications like high-end medical applications and service bureaus.

Other technologies may be used to measure the geometry of the undersurface of the object to be measured, such as a foot. These technologies include (1) contact digitizing wherein gauge pins spaced at known intervals are urged upward beneath the foot and sample the contour periodically, and (2) optical triangulation where radiation of a known characteristic is projected against the subject foot such that the resulting shape of the radiation as it contacts the foot is observed by a sensor, typically a camera. A processor is used to evaluate the observed image to determine the contour data of the object (e.g., the foot) being measured.

Contact digitizing is generally the preferred method of obtaining the underside of a foot when the merits of the resulting data are the exclusive criterion. A contact digitizer supports the foot while measuring. Supporting the foot allows a full weight bearing measurement to be made, while not allowing the foot to completely collapse against the flat, top surface of the scanner. This yields a supportive data set that captures the extension of the foot when weight is applied.

A laser scanner has a clear plate between the scanning mechanism and the subject being measured. In the instance of measuring a foot, if the foot is suspended above the glass plate the data produced by the scanner matches the shape of the foot. However, this technique requires that the foot be measured in an unweighted position. The contour data obtained from the foot in the unweighted position is not very desirable since the foot can expand by as much as size and one-half when weight is applied thereto in the course of walking. The contour produced by an unweighted measurement will oversupport the foot and cause discomfort. Yet, if the foot is placed against the clear plate to simulate the weight bearing of the foot, the bottom of the subject foot is completely flat. This produces an uncomfortable and unnatural, distorted shape.

Laser scanners also have a number of other problems associated with placing the foot against the clear plate such as (1) fogging where, if the foot is not completely dry, a fog is produced on the glass that tends to compromise the measurement accuracy of the foot since the shape of the subject foot is at least partially obscured by the fog; and (2) surface refraction caused by a lack of contrast of the subject foot due to, for example a light skin tone of a bare foot placed against the clear glass plate that disperses the projected radiation when it contacts the foot. The projected light disperses inside the body. It then refracts back through the clear plate. This produces an ambiguous radiation observation, as the radiation is diffused.

Accordingly, there is a need for a system that obtains a impression of the plantar surface of the foot coupled with the advantages of a laser scanning systems, as discussed above. Such a system would be of similar efficacy in acquiring data from any kind of medium used to capture a foot impression.

Alternative mediums to the use of foam for obtaining an impression of the foot, and particularly the plantar surface of the foot, also exist. One such common alternative medium is a sock casting, often called a "slipper cast". This technique involves encasing the foot in a casting material that hardens when activated. Once hardened, the casting is cut and removed from the foot. Removing the top portion of the casting then produces an impression of the foot. At that point it can be processed identically to a foam impression using a scanner.

SUMMARY OF THE INVENTION

This disclosure provides for an impression scanner system having improved calibration having a housing and a calibration plate of known geometry. The calibration plate has a plurality of different shapes thereon. The system also has a radiation source for emitting radiation towards the shapes on the plate and a surface for reflecting images created by the radiation on the shapes. A sensor for receiving the images of the shapes as the plate moves relative to the housing is also provided. A processor compares known geometry of the plate to the images received by the sensor and calibrates the sensor based upon the known geometry and images to reduce system aberration and distortion.

A scanner system for capturing an impression having improved calibration includes an object of known geometric values having a plurality of different shapes thereon and a radiation source for emitting radiation towards the plurality of different shapes. The system also provides for a surface for reflecting an image of the plurality of different shapes and a sensor for capturing reflected images of the plurality of different shapes and for outputting data responsive to the image of the plurality of different shapes. A processor that compares the outputted data to the known geometric values of the object and stores differences between the data and the values to minimize aberration of scanned objects.

A method of measuring the contour of an impression provides for calibrating a sensor using a plate having a plurality of different shapes thereon to derive calibration data and placing an object against in a medium to obtain an impression of the object. The method provides for scanning the impression with radiation emitted from a radiation source and sensing reflected light from the impression during the scanning and calculating spatial values representing the contour of the impression using the derived data from the calibration of the sensor.

BRIEF DESCRIPTION OF THE DRAWINGS

Other and further benefits, advantages and features of the present invention will be understood by reference to the following specification in conjunction with the accompanying drawings, in which like reference characters denote like elements of structure and.

DETAILED DESCRIPTION OF THE PREFERRED EMBODIMENT

The present invention provides a novel architecture for laser scanning. The embodiment described herein is designed to be illustrative of the architecture rather than a comprehensive, exhaustive listing of all possible implementations of the present invention.

The present invention preferably uses inexpensive components and technologies. These include, for example commodity cameras such as those used with personal computers (i.e., a digital camera). Such cameras are relatively inexpensive and designed for easy interfacing with a computer.

The camera used in an illustrative and exemplary application of the present invention can be a commercially available "webcam". The camera connects to a personal computer using a USB, serial, or other (preferably standardized) interface. The camera is preferably equipped with a pass filter. The filter can be a band-pass, high-pass, or low-pass filter to allow the passage of the desired spectrum of the radiation (e.g., light) of the structured emission source to pass through to the camera, but rejecting to a great degree other emissions that may come into the camera's view. For example, the camera can be outfitted with a filter to reject ambient light that may come into the field of view of the camera.

In one aspect hereof, a structured emission source is provided by a laser diode having a convex plastic lens at the emission end of the laser. The lens spreads the laser emission outwards in an axis to produce a line on a surface intersected by the laser emission. Laser diodes are relatively inexpensive and are also widely available.

The present invention is preferably compatible with and uses standard computing interfaces and communication protocols, thereby facilitating connection to commercially available computers and other processing peripherals using standard communication interface protocol(s). The USB interface is one such interface, as it is ubiquitous and requires little or no special skills to connect to. The ease of connection makes the present invention all the more useful. The USB interface facilitates use of an off-the-shelf, commercially available digital camera having a USB interface.

In an aspect of the present invention, an interface was designed to allow the USB connection to be used for the control of miscellaneous functions of the compact optical contour digitizer of the present invention. This aspect of the present invention contributes towards maintaining low costs and improves the practicality and reliability of the present invention.

The control electronic aspects of the present invention provide for control of motion along an axis, control of the radiation source, positioning control, and control of projection means used to illuminate the subject matter having its contour digitized. The projection means allows for direct imaging of the subject matter, as well as contour measurement. Direct imaging is desirable to derive metrics of the subject matter. In one aspect hereof, metrics are used to determine a length and a width of the foot (or any other subject matter being measured).

As discussed above, measuring an unweighted foot does not provide a complete set of data desirable for fully capturing the contour of the foot since the foot expands when weighted. Also, placing the foot on the glass plate of the scanner introduces other problems (e.g., fogging and over-flattening of the foot). Yet it is desirable to fully understand the contour of a weighted foot for the purpose of, for example, manufacturing customized orthotic supports.

Figure 1:
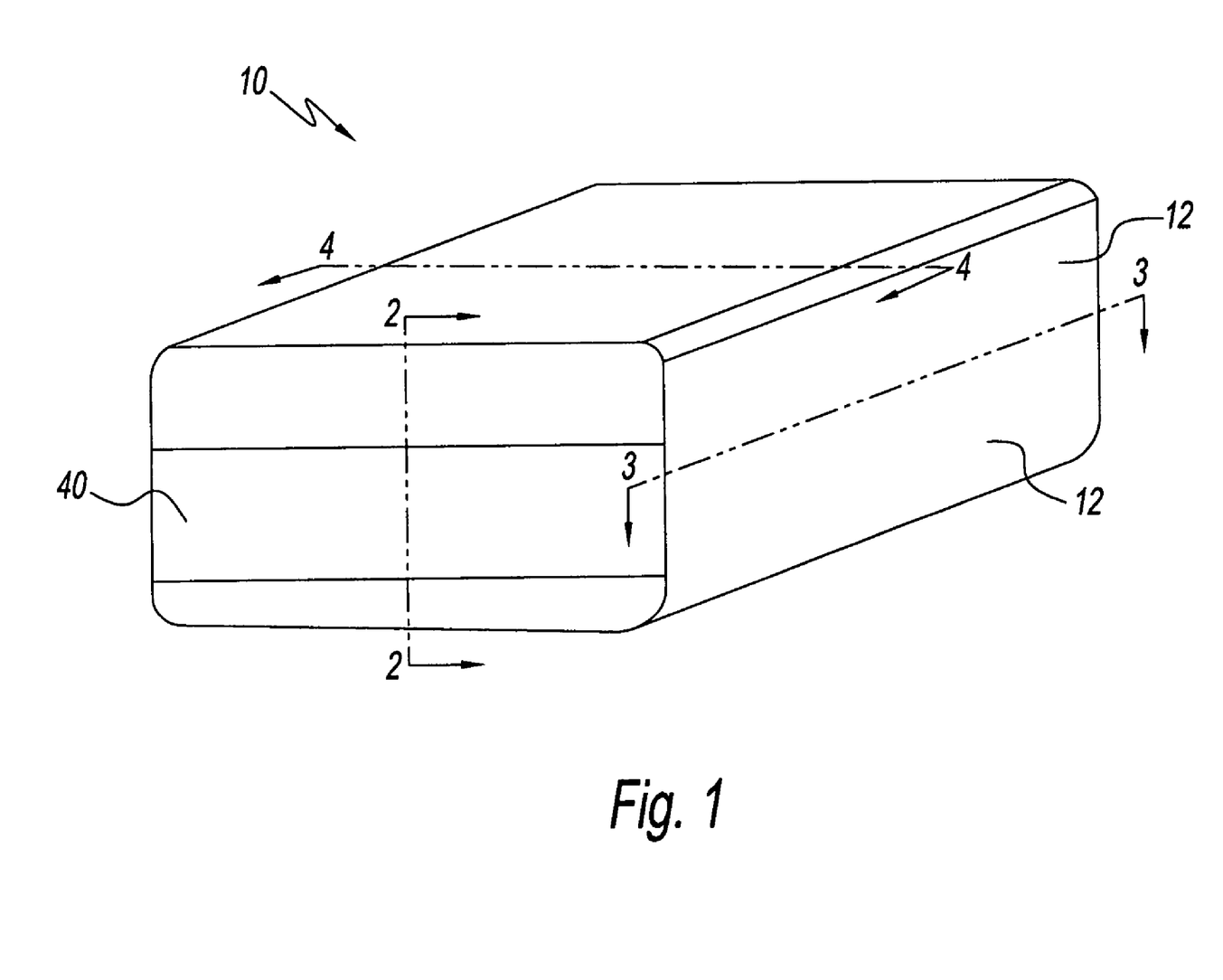
FIG. 1 illustrates a perspective view of the system according to the present invention.

The embodiment shown in FIG. 1 is a contour digitizer designed to measure the shape of the plantar surface of a human foot. This particular application of the present invention uses the digitizer to measure the foot for the purpose of fabricating an orthosis for the foot.

Figure 2:
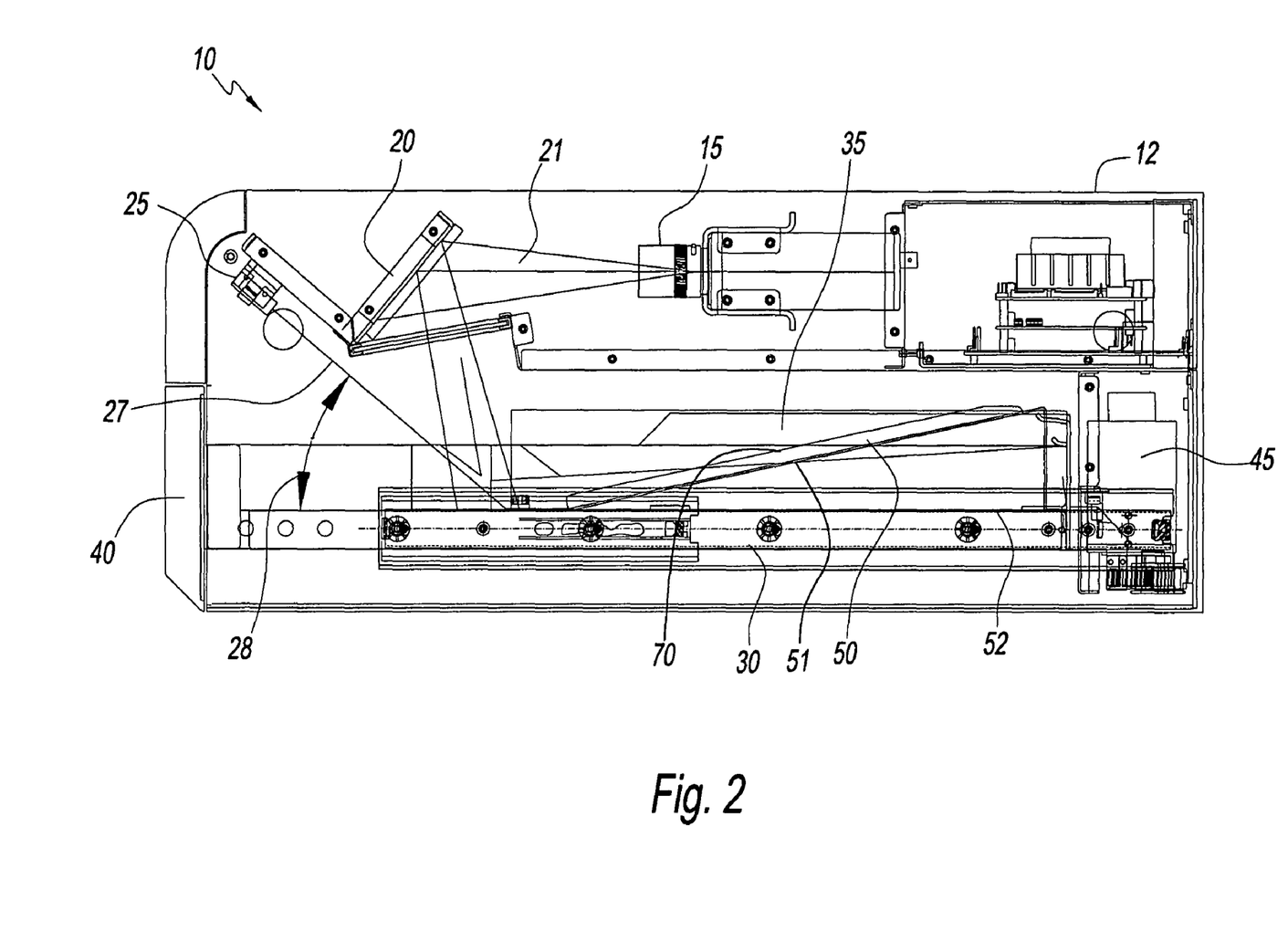
FIG. 2 illustrates a section view of the system of FIG. 1 taken along line 2-2, according to the present invention.
Figure 3:
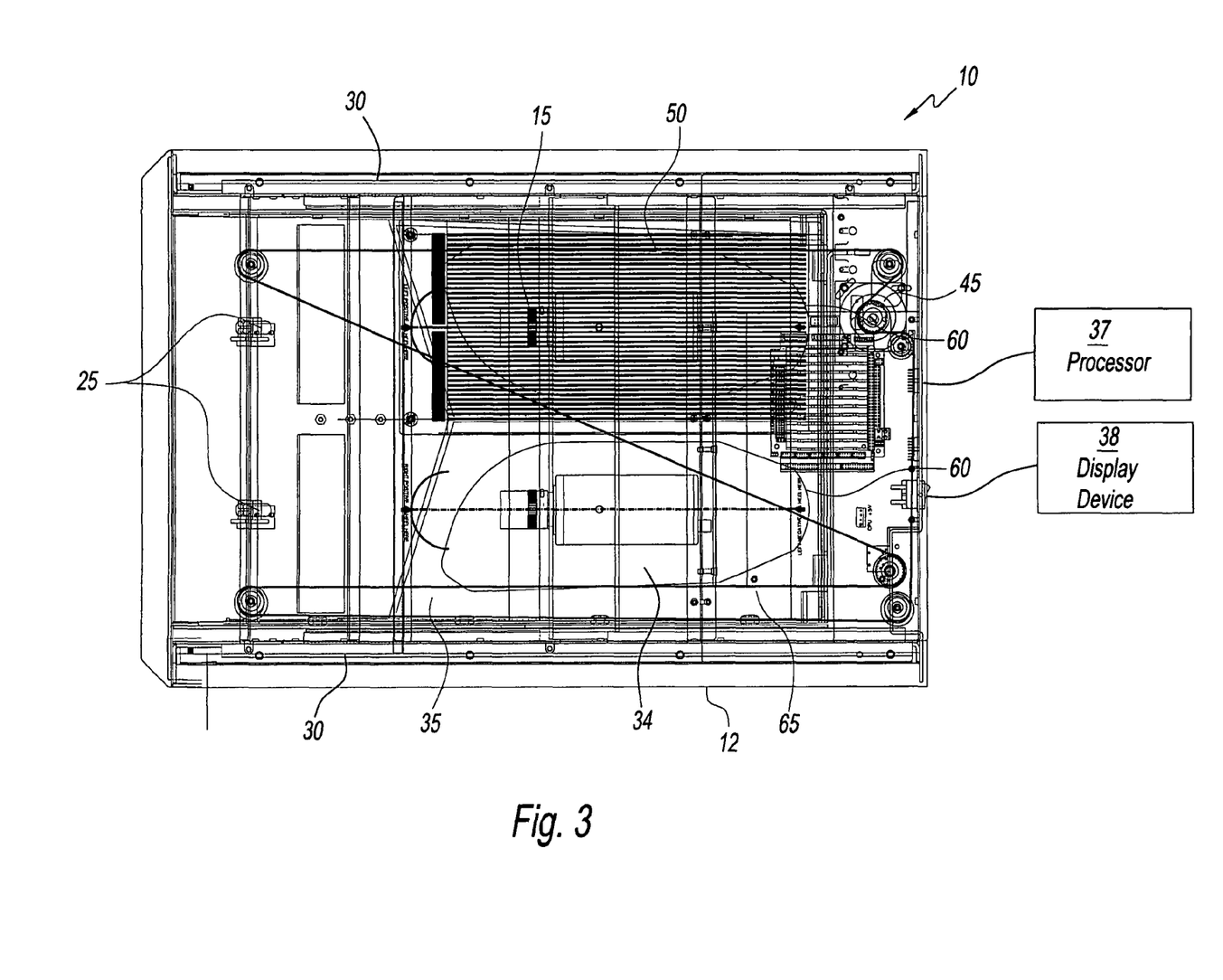
FIG. 3 illustrates a section view of the system of FIG. 1 taken along line 3-3, according to the present invention.

Referring to the figures and, in particular to FIGS. 1 through 3, a perspective view and section views, respectively, of the scanning system according to the present invention are shown and referenced generally using reference numeral 10. System 10 has a housing 12 that contains a pair of sensors such as, for example, cameras 15, a pair of reflective surfaces, such as mirrors 20, and a pair of radiation sources for emitting radiation. Radiation sources are preferably laser line generators 25. Laser line generators 25 each include a laser diode having a convex plastic lens at the emission end. The lens spreads the laser emission outwards in an axis to produce a line 27 against either a calibration plate or an impression that will be discussed below. The present disclosure has particular application to measuring the plantar surface of the foot for the purpose of fabricating orthotics for the foot. While radiation source is shown as a laser line generator 25, other devices such as photodiodes, a light, an infrared generator and an acoustic wave generator are also within the scope of this invention. While sensors are shown as being cameras, other sensors such as for example digital camera, a photodiodes and CCDs, could also be used.

System 10 contains a pair of multi-part sliding tracks 30 that are connected to inner surface of opposite sides of housing 12. A drawer 40 slides in tracks 30 for smooth movement relative to housing 12. Drawer 40 carries foam block 34 housed in containers 35 of drawer 40. Foam block 34 is preferably phenolic foam, an ultra low density expanded polystyrene material commonly used for insulation that is a pressure sensitive material which compress when a person's feet are pressed into containers 35. Foam block 34 is easily deformed, with little or no memory, and retains the deformed shape of impression 36 indefinitely. A slipper casting could also be used to capture the contour of the plantar surface of a foot. A slipper casting would also retain a negative impression of the plantar surface of the foot for orthotics manufacture. Motor 45 provides the motive force to enable drawer 40 to slide via sliding track 30 to move foam containers 35.

Figure 4:
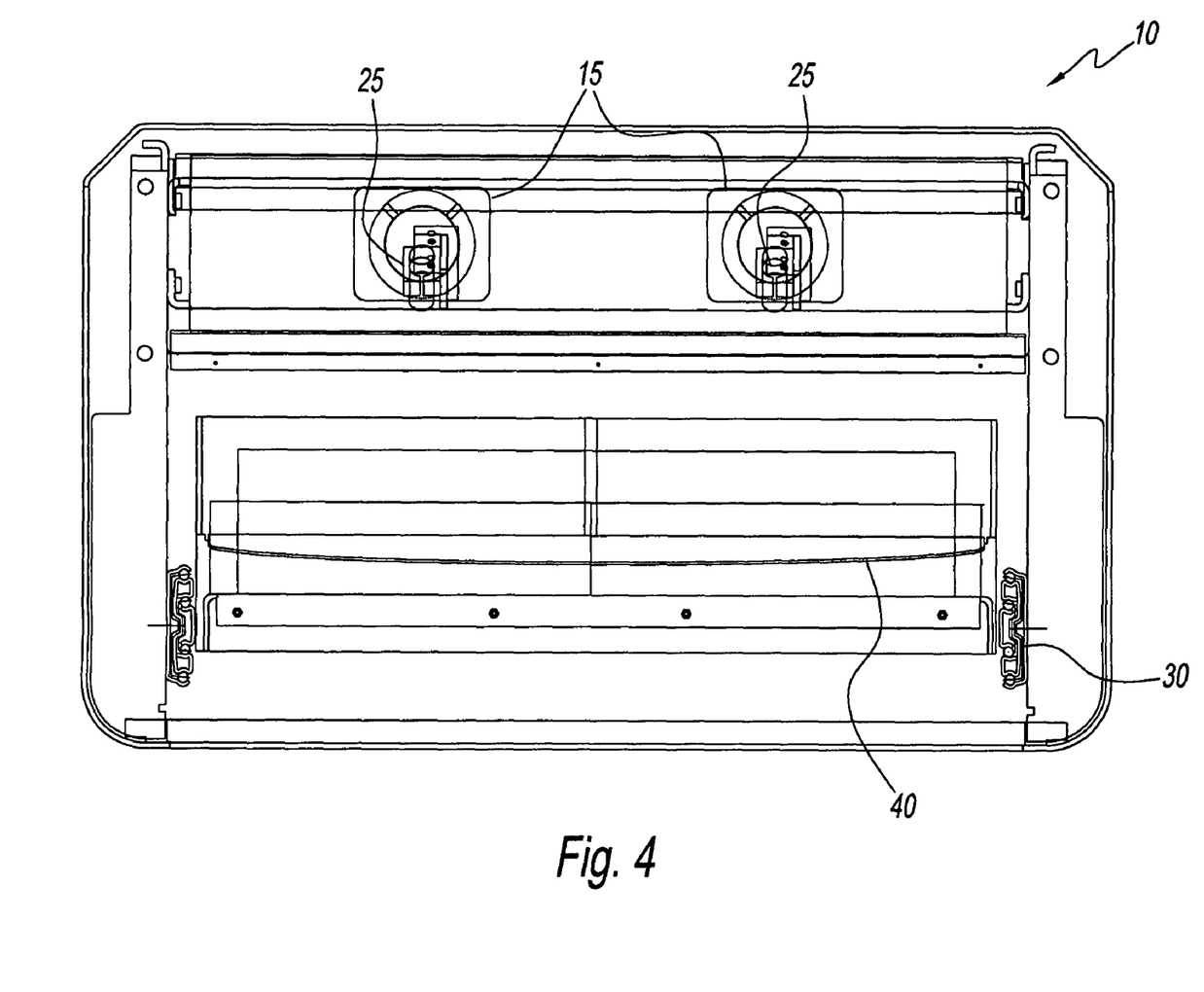
FIG. 4 illustrates a section view of the the system of FIG. 1 taken along line 4-4, according to the present invention.
Figure 5:
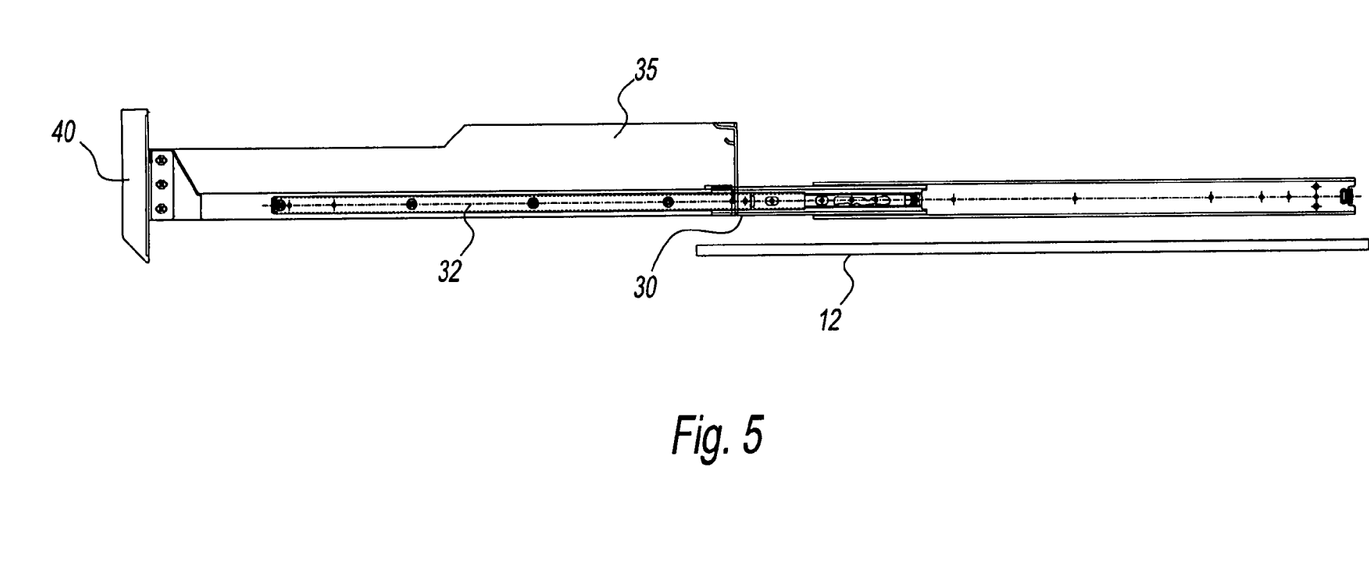
FIG. 5 illustrates a side view of the sliding mechanism of the system, according to the present invention.
Figure 6:
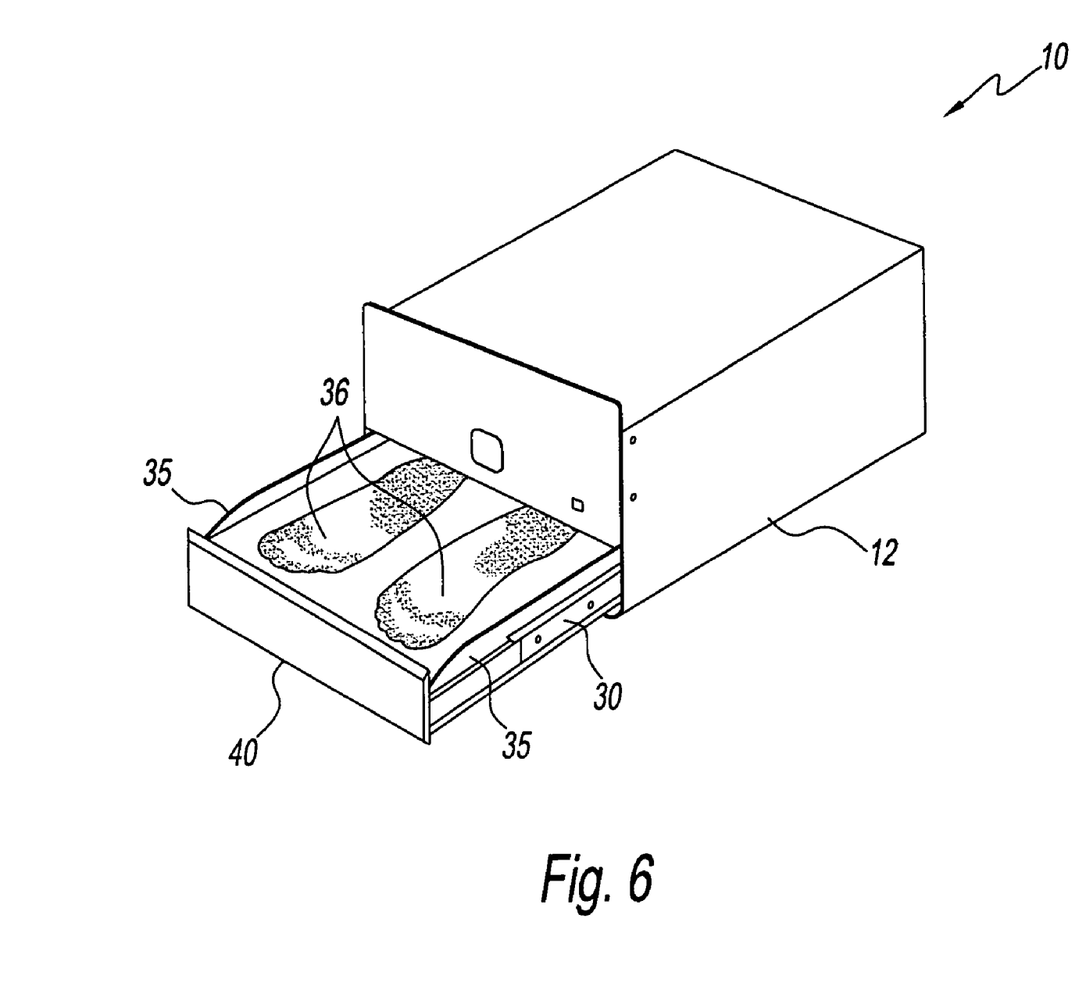
FIG. 6 illustrates a perspective view of the system of the present invention with the drawer in an extended position.

FIG. 3 also shows two templates 60 on which a user may place her feet in the respective foam containers 35. Additionally, as shown in FIG. 4, various connection ports are also associated with system 10 for electrical connection with processor 37 and/or graphical display device 38 to compute and graphically present, respectively, the results of the scanned foam impression 36 in the foam containers 35. The present invention is preferably compatible with and uses standard computing interfaces and communication protocols, thereby facilitating connection to commercially available computers and other processing peripherals using standard communication interface protocol(s).

FIGS. 2 through 6 show the positioning of drawer 40 inside housing 12. Cameras 15 and laser liner generators 25 are positioned almost directly above respective foam blocks 34 in containers 35. Drawer 40 supports foam containers 35 during the measurement process and during storage. As shown in FIG. 2, drawer 40 moves in sliding tracks 30 of FIG. 5 using a series of ball bearings, although other friction minimizing methods could also be used. Sliding tracks 30 are on each side of housing 12. Each track 30 has an inner component and an outer component 32. Inner component is affixed to drawer 40 and outer component is affixed to housing 12. Inner component and outer component 32 slide relative to one another to insure that full extension of drawer 40 from box 10 is possible. This configuration also ensures that the entire length of foam block 34 within foam container 35 will be scanned. Significantly, tracks 30 also conserve space reduce overall length of system 10 for more convenient use.

Generally, aberration and distortion that occurs in cameras causes physical points of equal distance apart captured in a camera image to appear to be non-equidistant. To compensate for this phenomenon the process of calibrating to known points across the entire width of the field of view compensates for such lens aberration and distortion.

Figure 7:
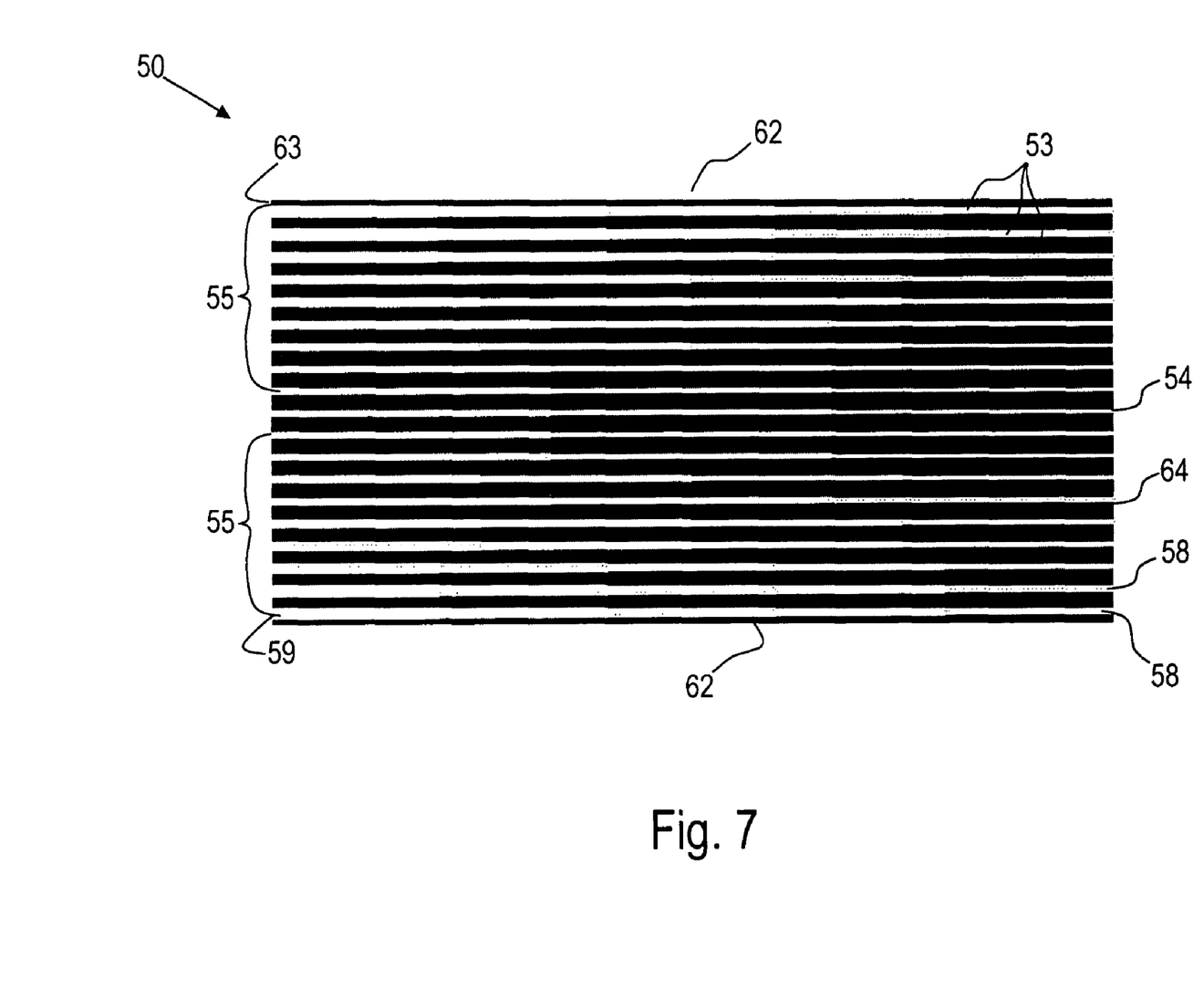
FIG. 7 illustrates a view of the calibration plate of FIG. 3, according to the present invention.

System 10 also has a calibration plate 50 having a plurality of high contrast different shapes, as shown in FIGS. 2 and 7. Inclined calibration plate 50 is marked with a plurality of different shapes that are exactly measured isosceles trapezoids 53 or gradually tapered lines. The axes of the plurality of trapezoids and lines are equidistant apart in real space but do not appear so in the image of camera 15. Mapping this difference across the width of the image minimizes the effect of lens aberration upon the scanned object. Plurality of trapezoids 53 include a central trapezoid 54 and lateral trapezoids 55 disposed on opposite sides of central trapezoid 54. Each of the plurality of trapezoids 53 extends along the entire length of plate 50. Each of the plurality of trapezoids 53 also has a base 58 and a top 59. Plate 50 has lateral edges 62, a top edge 63 and a bottom edge 64. Base 58 and top 59 are parallel. Top 59 has a shorter dimension than base 58, thus creating a taper in each of the plurality of trapezoids at the top edges closest to cameras 15. Each of the plurality of trapezoids 53 is filled with a highly reflective color. In contrast, the area surrounding and between each of the plurality of trapezoids 53 is colored to be non-reflective. During the scanning process line 27 that is projected against plate 50 will be received by camera as a series of white dots or points, representing the reflected portions of each of the plurality of trapezoids.

The spacing and shape of each of the plurality of trapezoids 53 on plate 50 reduces aberration and distortion that is due lens of camera 25. A central trapezoid 54 of the plurality of trapezoids 53 is placed exactly in the physical center of plate 50 at a central axis thereof. Central trapezoid 54 and each of the lateral trapezoids 55 has a central axis that is equidistant from the axes of adjacent trapezoids. While the axes of the plurality of trapezoids 53 have an equidistant spacing, lateral trapezoids 55 that are progressively closer to lateral edges 62 have broader bases 58, and are thus wider. Thus, the image of points that are observed by camera 15 of the points from the lateral trapezoids will be appear brighter than they would if they were not broadened. The broadening of lateral trapezoids 55 compensates for dimming on the lateral edges of images due to lens aberration.

The shape of each of the plurality of trapezoids 53 also compensates for the disproportionate brightness of images from the points of the trapezoids closest to camera 15. The reflected brightness of line 27 from inclined plate 50 is non-linear relative to the distance of plate 50 to the camera 15. Plate 50 of the present invention compensates for this distorted appearance so that the images of points received by the cameras 15 during calibration will have uniform brightness and size for greater resolution and accuracy. The compensation in size of reflected image points will compensate for the greater brightness that is received by images that are closer to the camera than those that are further away.

Thus, the trapezoidal shapes on calibration plate 50 compensate for aberration as well as disproportionate appearance of brightness and size of reflected points.

Calibration plate 50 is positioned at a predetermined angle 51 from the horizontal defined by base plate 52 in drawer 40. In this embodiment of the invention, angle 51 is approximately 12° from the horizontal. Predetermined angle 51 of calibration plate 50 and the size of the image field of view 21 as observed by camera 15 will determine the maximum possible scanning height or depth of the impression. While a large angle 51 relative to base plate 52 allows for a higher maximum calibrated height or depth of the impression, field of view 21 that can be observed by camera 15 may be limited. As predetermined angle 51 increases, a loss of resolution occurs because fewer points created by line 27 against plate 50 from the scanning process can be captured in a longitudinal direction of movement. Conversely, a shallow angle, while providing a large field of view 21, may not offer as great a level of perspective from which to collect images of points for mapping during calibration. Thus, angle 51 of plate 50 varies for the specific requirements of an impression or size of drawer 40. While angle 51 is variable, it is preferably between a range of 8° and 25° relative to the horizontal or base plate 52.

Calibration plate 50 is movable in order to accommodate multiple cameras as well as different impressions or drawer sizes. System 10 also has a belt 65 operatively associated with motor 45 to enable controlled linear advancement of drawer 40 and foam container 35 on sliding track 30 during laser scanning.

The operation of system 10 according to the present invention will now be addressed in conjunction with other aspects of the present invention, as with reference to FIGS. 1 through 7. Foam containers 35 each contain a foam block 34, such as, for example, phenolic foam, that is easily deformed. Alternatively, a casting from a slipper casting could also be placed in drawer 40 for scanning. When drawer 40 is pulled away from housing 12, the user places her feet in the respective containers 35 to provide an impression 36 in block 34 of the plantar surfaces of the feet. The feet must be placed in a crossed-over fashion to prevent excessive pressure from being applied in any one of the foam containers 35. Such excessive pressure could yield inaccurate scanning results that would potentially result in improperly fitted orthotics. After the user removes her feet from the foam containers 35 and impressions 36 have been made in foam block 34, drawer 40 is fully re-positioned in housing 12. Foam block 34 retains the contour of impressions 36 of plantar surface of the foot for scanning at a later time.

Prior to scanning unknown geometries, a calibration to a known geometry is required for each camera/laser unit. This calibration is needed only once per unit the lifetime of the device. Before calibration, the calibration plate 50 is secured in drawer 40. Motor 45 and belt 65 can be selectively activated to move drawer 40 and thus foam containers 35 away from housing 12. Belt 65 moves drawer 40 containing calibration plate 50 at a selected rate precisely in a longitudinal direction directly under laser line 27 and camera 15. Laser line generator 25 generates a line 27 that is projected against calibration plate 50 at a predetermined angle of incidence 28. Predetermined angle 28 is determined within a possible range of angles in order to accommodate the necessary depth of the impression and to minimize the loss of visible object surface due to shadowing.

As calibration plate 50 moves relative to line 27, reflected points are visible in the mirror 20 and captured as images by camera 15 as they come in field of view 21. Computer vision software processes each image to locate the previously described points produced by plurality of tapered trapezoids 53. Because the center axis of each of the plurality of shapes is at a known position in three-dimensional space, the pixel position of its rendering in the camera image can be used to represent that three-dimensional point. By obtaining a series of images while traversing plate 50 along its length, each possible pixel in camera field of view 21 is mapped to an actual point in three-dimensional space using known trigonometric functions. Thus a calibration map is developed and saved in persistent storage of scanning system 10 as a data lookup table. Software can load the table at any time, providing rapid data lookups to retrieve the physical point in space for any point in subsequent images. In this way, when laser line 27 projects upon an unknown object such as an impression, the reflection of that line can be found by software in the camera image and translated into three-dimensional points in space using data lookup table. Thus calibration of any camera/laser unit is required only once per lifetime of the device, as long as persistent storage of the calibration map remains intact. After calibration, plate 50 is removed.

It is to be understood that the scanning system of the present invention includes storage as well as processing and applications to carry out the present invention.

After contour of impressions 36 have been made and are returned to housing 12, scanning commences. Laser line generator 25 projects a line across an approximately 6 inch width of impression 36 in foam block 34. Mirror 20 is used to fold or reflect view 21 observed by camera 15 of the projection of laser line 27 against contour in foam block 34. By folding view 21, the overall dimensions of the housing, both height and length, are greatly reduced. In addition, the use of mirror 20 enables a longer focal length and allows the use of less expensive camera optics and minimizes aberrations. In the present application, the scanning system 10 acts directly on the impression 36 left by the foot within foam container 35. Camera 15 supplies an image used to read the position of the laser line 27 on impression 36. The contour of impression is captured and the spatial orientation of points that are received by camera 15 are stored by system 10. The development of contour is computed by using the found laser points in the image to look up the corresponding three dimensional spatial point in the calibration map.

Generally, scanning of one contour completes with inward drawer traversal, and scanning of the second contour completes with outward drawer traversal.

Significantly, the size and geometry of system 10 is designed such that line 27 reflects as a series of horizontal points across the center of the camera field of view 21 at the mid-height 70 of the inclined calibration plate 50. As well, this design ensures that the middle of field of view 21 correlates to 50% of the dynamic range, or depth of impression, for data acquisition. When light beam 27 is focused at a location of calibration plate 50 that correlates to half of the depth of the impression, not only is the aberration reduced, but also the entire impression can be viewed in a single pass of drawer 40. The efficiency of scanning system 10 is optimized by having the middle of field of view located at this position.

System 10 allows accurate calibration and subsequent quick and precise scanning of the plantar surface of the foot without the use of plaster. Additionally, the scanning can be performed by a single unitary device to save time and expense for the manufacture of orthotics. Further, the calibrating system compensates both for camera lens aberration in the image of the field of view 21, as well as non-linear brightness of points in the image due to varying distance of calibration plate 50 from camera 15.

The present invention having been thus described with particular reference to the preferred forms thereof, it will be obvious that various changes and modifications may be made therein without departing from the spirit and scope of the present invention as defined in the appended claims.

We claim:

1. An impression scanner system having improved calibration comprising:
   a housing;

a calibration plate of known geometry disposed in said housing; said calibration plate having a plurality of different shapes thereon;

a radiation source for emitting radiation towards said shapes on said plate;

a surface for reflecting images created by said radiation on said shapes;

a sensor for receiving said images of said shapes as said plate moves relative to said housing; and a processor that compares known geometry of said plate to said images received by said sensor and calibrates said sensor and radiation source based upon the known geometry and said images.

2. The system of claim 1, wherein said plurality of different shapes are a plurality of tapered lines or a plurality of trapezoids that taper along a longitudinal length of said plate.

3. The system of claim 1, wherein said radiation source is selected from the group consisting of: a laser line generator, a photodiode, a light, and an infrared generator.

4. The system of claim 1, wherein said sensor is selected from the group consisting of a camera, a digital camera, a photodiode and a CCD.

5. The system of claim 1, wherein said plurality of different shapes comprise a centrally disposed shape and laterally disposed shapes spaced from said centrally disposed shape on said calibration plate, said laterally disposed shapes being progressively broader away from said centrally disposed shape.

6. The system of claim 5, wherein said centrally disposed shape and said laterally disposed shape each has a center line that is equidistant from a centerline of others of said plurality of different shapes.

7. A scanner system for capturing an impression having improved calibration comprising:

an object of known geometric values having a plurality of different shapes thereon;

a radiation source for emitting radiation towards said plurality of different shapes;

a mirror for reflecting an image of the said plurality of different shapes;

a sensor for capturing a reflected image of said plurality of different shapes and for outputting data responsive to said image of said plurality of different shapes, a processor that compares said outputted data to said known geometric values of said object and stores differences between the data and the values, wherein said differences are used to minimize aberration of scanned objects.

8. The system of claim 7, wherein said radiation source is selected from the group consisting of: a laser line generator, a photodiode, a light, and an infrared generator.

9. The system of claim 7, wherein said sensor is selected from the group consisting of a camera, a digital camera, a photodiode and a CCD.

10. The system of claim 7, wherein said object of known geometry comprises a calibration plate.

11. The system of claim 10, wherein said emitted radiation impinges said plate at a predetermined angle of inclination.

12. The system of claim 10 wherein said angle is selected to impinge said plate at a mid-point of said plate that corresponds to half of the height of the impression to be captured.

13. The system of claim 7, wherein said plurality of shapes comprise a plurality of trapezoids or tapered lines.

14. The system of claim 13, wherein centerlines of each of said plurality of trapezoids or tapered lines are mutually equidistant.

15. The system of claim 13, further comprising a housing that receives a drawer, wherein said calibration plate is received in said drawer.

16. The system of claim 15, wherein said drawer is movable relative to said housing to move said calibration plate relative to said emitted radiation.

17. The system of claim 15, wherein said object is disposed at predetermined angle in said drawer.

18. The system of claim 17, wherein said angle is from approximately 8° to 25°.

19. A method of measuring the contour of an impression, the method comprising the steps of:
   a) calibrating a sensor and a radiation source using a plate having a plurality of different shapes thereon,
   b) placing an object against in a medium to obtain an impression of said object;
   c) scanning the impression with radiation emitted from a radiation source;
   d) sensing reflected light from said impression during said scanning; and
   e) calculating spatial values representing the contour of the impression using measured data derived from the calibration of the sensor and the radiation source.

20. The method of claim 19, wherein said plurality of different shapes are a plurality of tapered lines or a plurality of tapered trapezoids that taper along a longitudinal length of said plate.

21. The method as recited in claim 19, wherein said step of calibration further comprises:

projecting radiation from a radiation source against a plate of known geometry;

reflecting images created by said radiation on said plate;

sensing said images as said plate moves relative to said radiation source and outputting signals of said images;

comparing the known geometry of said plate to said outputted signals; and storing the differences between the known geometry and said outputted signals to minimize aberration of scanned objects of unknown geometry.

22. The method of claim 21, wherein said plate has plurality of tapered lines or a plurality of trapezoids thereon.

23. The method of claim 21, wherein said plurality of different shapes comprise a centrally disposed shape and laterally disposed shapes spaced from said centrally disposed shape on said calibration plate, said laterally disposed shapes being progressively broader away from said centrally disposed shape.

24. The method of claim 23, wherein said centrally disposed shape and said laterally disposed shape each has a center line that is equidistant from a centerline of others of said plurality of different shapes.

* * * * *